United States Patent
Taylor

(10) Patent No.: US 9,795,366 B2
(45) Date of Patent: Oct. 24, 2017

(54) BIO-ABSORBABLE WOUND CLOSURE DEVICE AND METHOD

(71) Applicant: Edwards Lifesciences Corporation, Irvine, CA (US)

(72) Inventor: David M. Taylor, Lake Forest, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 129 days.

(21) Appl. No.: 14/490,334

(22) Filed: Sep. 18, 2014

(65) Prior Publication Data

US 2016/0081680 A1    Mar. 24, 2016

(51) Int. Cl.
*A61B 17/00* (2006.01)
*A61B 17/12* (2006.01)

(52) U.S. Cl.
CPC ..... *A61B 17/0057* (2013.01); *A61B 2017/00004* (2013.01); *A61B 2017/00243* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61B 2017/00654* (2013.01); *A61B 2017/00659* (2013.01); *A61B 2017/00867* (2013.01)

(58) Field of Classification Search
None
See application file for complete search history.

(56) References Cited

U.S. PATENT DOCUMENTS

| | | |
|---|---|---|
| 5,437,631 A | 8/1995 | Janzen |
| 5,496,332 A | 3/1996 | Sierra et al. |
| 5,545,178 A | 8/1996 | Kensey et al. |
| 5,951,589 A | 9/1999 | Epstein et al. |
| 5,964,782 A | 10/1999 | Lafontaine et al. |
| 6,022,361 A | 2/2000 | Epstein et al. |
| 6,056,769 A | 5/2000 | Epstein et al. |
| 6,056,770 A | 5/2000 | Epstein et al. |
| 6,464,712 B1 | 10/2002 | Epstein et al. |
| 6,592,547 B2 | 7/2003 | Grimes et al. |
| 7,044,982 B2 | 5/2006 | Milbocker |

(Continued)

FOREIGN PATENT DOCUMENTS

WO    0033744 A1    6/2000

OTHER PUBLICATIONS

Int'l. Search Report for PCT/US2015/051002, dated Dec. 21, 2015.
Extended Search Report for European Application No. 15842468.9 dated Aug. 22, 2017.

*Primary Examiner* — Shaun L David
(74) *Attorney, Agent, or Firm* — Klarquist Sparkman, LLP

(57) ABSTRACT

A wound closure device comprises a first frame and a flexible tubular section connected to the first frame, the first frame implantable through a wound in a patient's skin into a lumen of a blood vessel with a portion of the tubular section extending out through the skin. The tubular section has a first portion and a second portion, a wall of the tubular section defining a coaxial inner bore. Twisting the first portion relative to the second portion of the tubular section closes the bore is closed in an area of the tubular section between the first and second portions, thereby closing the wound. Also disclosed is an embodiment for closing an opening in a heart, as well as a delivery device, systems, and methods.

11 Claims, 12 Drawing Sheets

(56) References Cited

U.S. PATENT DOCUMENTS

| | | |
|---|---|---|
| 7,753,925 B2 | 7/2010 | Mialhe |
| 8,083,768 B2 | 12/2011 | Ginn et al. |
| 2001/0037053 A1* | 11/2001 | Bonadio ............ A61B 17/0293 600/208 |
| 2003/0153935 A1 | 8/2003 | Mialhe |
| 2006/0058820 A1* | 3/2006 | Mialhe ............... A61B 17/0057 606/157 |
| 2008/0051830 A1 | 2/2008 | Eidenschink et al. |
| 2010/0016885 A1 | 1/2010 | Eidenschink et al. |
| 2010/0114156 A1* | 5/2010 | Mehl ................. A61B 17/0057 606/213 |
| 2011/0034954 A1 | 2/2011 | Tan et al. |
| 2011/0260449 A1* | 10/2011 | Pokorney ............... A61B 17/11 285/321 |
| 2012/0065675 A1 | 3/2012 | Kolb |
| 2012/0083832 A1 | 4/2012 | Delaloye et al. |
| 2012/0109189 A1* | 5/2012 | Voss ................... A61B 17/0057 606/213 |
| 2012/0253386 A1* | 10/2012 | Rowe ................ A61B 17/0293 606/213 |
| 2012/0271348 A1 | 10/2012 | Tekulve et al. |
| 2013/0190812 A1 | 7/2013 | Vidlund |
| 2013/0226229 A1 | 8/2013 | Uchida et al. |
| 2013/0253577 A1 | 9/2013 | Tegels |
| 2013/0282053 A1 | 10/2013 | Rideout |
| 2014/0114345 A1* | 4/2014 | Ciobanu ............ A61B 17/0057 606/213 |

* cited by examiner

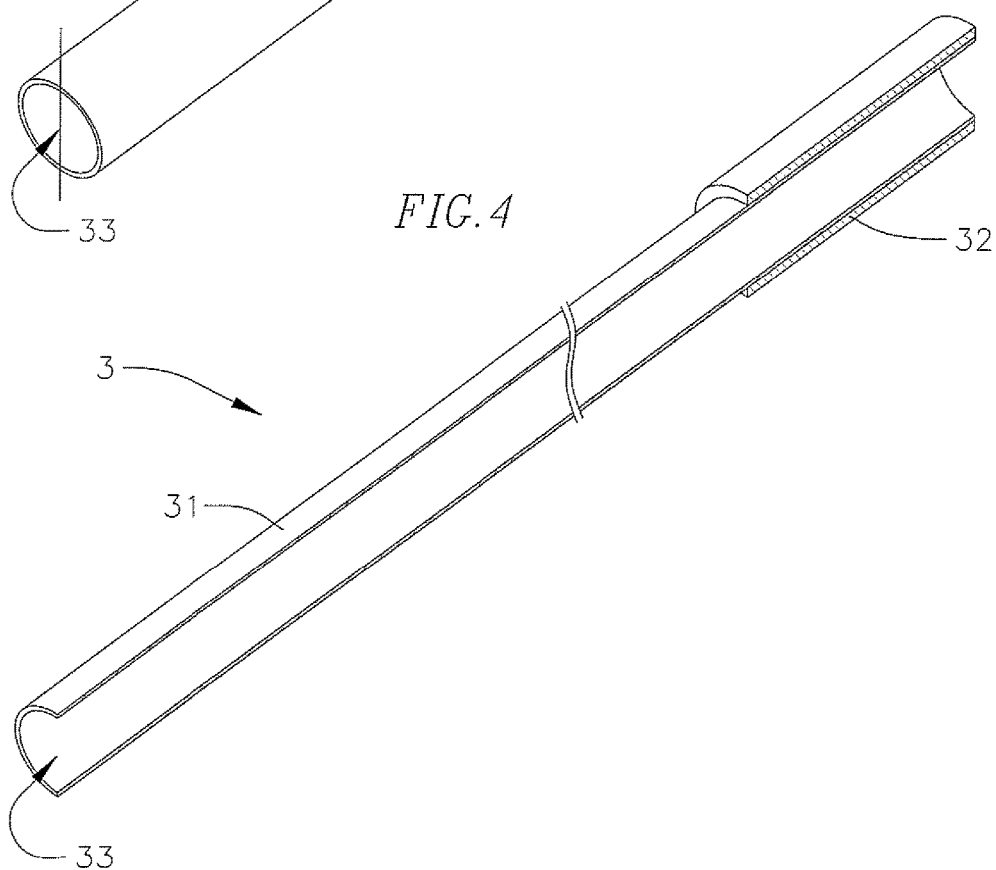

BIO-ABSORBABLE WOUND CLOSURE DEVICE AND METHOD

BACKGROUND

Field

The present application concerns wound closure devices and methods of implanting the devices. The wound closure devices and methods can be used for percutaneous occlusion of large vascular access sites in the human body. Embodiments of the wound closure device may be used to occlude vascular access sites that are, for example, larger than about 14 French in diameter. The wound closure devices and methods can also be used for occlusion of other access sites, for example, through a wall of a heart such as an apical access site of a heart.

Description of Related Art

Various procedures that are performed on a patient's vascular system and/or heart are performed percutaneously and via an arteriotomy hole or vascular access site. Upon completion of such procedures, the arteriotomy hole or vascular access site must be occluded or closed. Some known occlusion methods include needle and suture methods, stapling methods, methods involving exterior compression, methods involving solid collagen plugs, and methods involving balloon occlusions and liquid collagen sealing. However, these and other known wound closure or occlusion methods may only occlude or close arteriotomy holes that are smaller than, for example, about 14 French, and may generally only be effective in occluding arteriotomy holes that are smaller than about 8 French.

The above methods are therefore limited to closing smaller vascular access sites. Furthermore, the procedures are complicated, and good occlusions or seals may still be difficult to obtain even for smaller openings.

As a result, while procedures such as percutaneous heart valve replacements can generally be performed minimally invasively, depending on the size of the vascular access site needed for the procedures, a more invasive follow-up procedure may still be required to effectively close the access site.

In other applications, access sites may be made directly in a wall of a heart, for example, at or near the apex of a heart. In these such applications, current sealing devices and methods may be similarly complex and relatively ineffective.

SUMMARY

Accordingly, there is a need to provide devices and methods for more effectively and less invasively closing large arteriotomy holes or vascular access sites. It is therefore an object of the invention to provide a wound closure device and a method for percutaneously closing large arteriotomy access sites, for example, access sites that are larger than about 14 French in diameter, and in some embodiments, access sites that are as large as about 24 French to about 30 French in diameter, or greater.

Another object of the invention is to provide a wound closure device and method that can also be applied percutaneously to an arteriotomy hole after various percutaneous procedures, such as, for example, retrograde delivery or replacement of a prosthetic heart valve. In some embodiments, such procedures are performed through, for example, the femoral artery, where embodiments of the wound closure device can be deployed to seal a large arteriotomy hole in the femoral artery.

There is also a need to provide devices and methods for more effectively closing access sites in heart walls, for example, apical access sites. It is therefore another object of the invention to provide a wound closure device and a method for more effectively closing access sites in heart walls, and more specifically, for closing apical access sites.

In accordance with the objects of the invention, embodiments of the invention provide percutaneous wound closure devices and methods for occluding large vascular access sites, for example, arteriotomy holes that are larger than about 14 French in diameter. Currently, while more invasive cutdown and repair methods have been studied for occluding larger vascular access sites, no previously known percutaneous procedures have successfully addressed this issue. Other embodiments of the invention provide wound closure devices and methods for occluding access sites in heart walls, for example, apical access sites.

Embodiments of the invention therefore provide devices and methods for a fast and safe closure of large vascular or heart access sites.

BRIEF DESCRIPTION OF THE DRAWINGS

The foregoing and other features and advantages of the invention will become apparent from the following detailed description of embodiments, by means of the accompanying drawings. In the drawings:

FIG. 3 is a perspective view of a delivery sheath according to an embodiment of the invention;

FIG. 4 is a cross-sectional view of the delivery sheath of FIG. 3;

DETAILED DESCRIPTION

Figure 1:
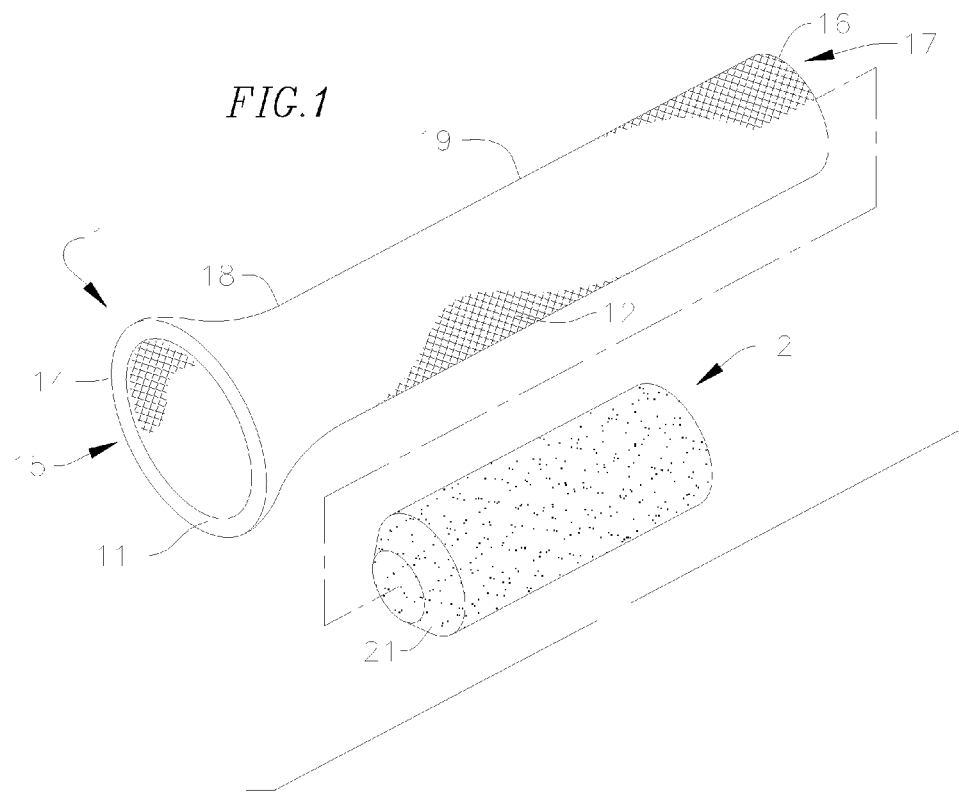
FIG. 1 shows a wound closure device according to an embodiment of the invention.

FIG. 1 shows a wound closure device according to an embodiment of the invention. The device includes a sealing or occluding means, for example, an implant 1 as illustrated in FIG. 1. The device may further include a plugging or stabilization means, for example, a plug 2 as further illustrated in FIG. 1.

The implant 1 has a longitudinal axis, a distal, first end 14 with a first opening 15 and a proximal, second end 16 with a second opening 17, where the distal first end is configured to be the leading end during implantation. In a resting or unstressed position, the second opening 17 is generally smaller than the first opening 15. The first end 14 of the implant 1 includes a frame or ring 11, which may be circular, oval-shaped, or ring-shaped, and may have a diameter of from about 30 French to about 35 French. In some embodiments, the ring 11 may be larger or smaller than from about 30 French to about 35 French, depending on the particular application. The ring 11 may be made of or include a bioabsorbable material, for example, any of the bioabsorbable polymers and materials discussed below. In some embodiments, the ring comprises a shape memory material, for example, nitinol and/or a shape memory polymer. The ring 11 is collapsible to a smaller size for advancement through a delivery means, such as a delivery sheath (e.g., the delivery sheath 3 illustrated in FIG. 3).

The implant 1 further includes an elastic tube, tubular section, or tubular portion 12 attached or affixed to the ring 11, the tube 12 comprising a first or distal portion 18 and a second or proximal portion 19. A wall of the tube 12 defines a bore or lumen, which is coaxial with the longitudinal axis in some embodiments. The tube 12 may have a resting diameter of from about 16 French to about 18 French, and may have a wall thickness of from about 0.01 inches (about 0.25 mm) to about 0.015 inches (about 0.4 mm), and an initial length of about 15 cm prior to implantation. The tube 12 may be arranged as a mesh, and/or may be made of a material that has a lower durometer or is softer than the material of the ring 11, and may also be made to be thinner than the ring 11. The tube 12 may also be made of or include a bioabsorbable material, and/or may be made of or include another soft material, for example, urethane, silicone, ethylene-propylene rubber, EPDM, fluoroelastomer, or the like. The tube 12 is attached or affixed to the ring 11, for example, by molding, adhering, and/or welding or by various other means, and the tube 12 may be stretched to fit the ring 11 at the attachment. The seal formed between the ring 11 and the tube 12 may prevent blood from flowing therethrough.

Each part of the implant may be made of a bioabsorbable polymer or other bioabsorbable material, for example, polyglycolide, polylactide, poly(s-caprolactone), poly(lactide-co-glycolide), or of various other bioabsorbable materials. The parts of the implant can be made of the same materials, or can be made of different materials.

Figure 2:
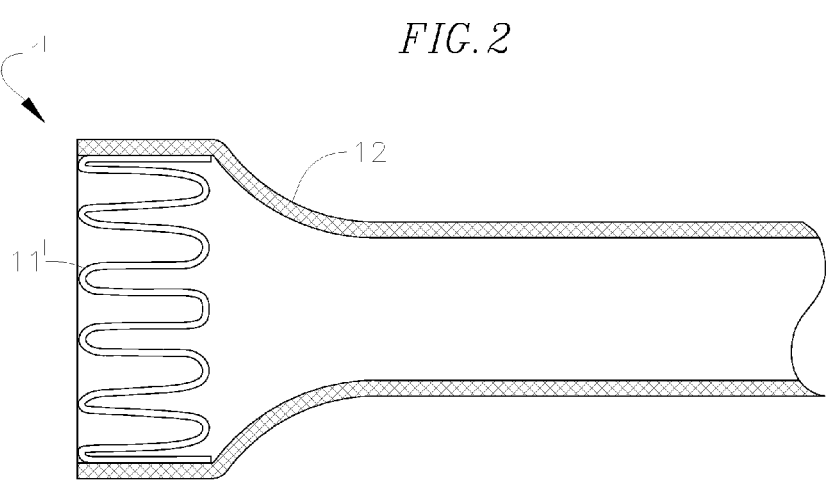
FIG. 2 is a cross-sectional view of an implant of a wound closure device according to another embodiment of the invention.

FIG. 2 is a cross-sectional view of an implant 1' of a wound closure device according to another embodiment of the invention. The implant 1' differs from the implant 1 of FIG. 1 in that the ring 11' in FIG. 2 is designed as a stent, for example, a single crown stent. The ring may alternatively be a multiple crown stent in other embodiments. The stent ring 11' may allow for more uniform crimping or compressing when the implant 1' is inserted into a delivery sheath. In some embodiments, the stent may also be configured to be flared or tapered towards one direction, to create a contour at the first end that reduces or minimizes intrusion into a blood vessel and/or reduces the obstruction of blood flow after implantation of the wound closure device.

Referring back to FIG. 1, the wound closure device may further include a plug 2. The plug 2 may be made of or include collagen, for example, a bovine collagen. In the illustrated embodiment, the plug 2 is substantially cylindrical in shape, and has a tapered or beveled end 21, which may facilitate insertion of the left side of the plug 2 into second opening 17 at the second end on the right side of the tube 12 as illustrated. The plug may be from about 0.5 inches (about 13 mm) to about 0.75 inches (about 20 mm) long and about 0.25 inches (about 6 mm) in diameter. Generally, the diameter of plug 2 will be greater than the resting diameter of the tube 12, so that advancement of the plug 2 through the tube 12 will effect a radially outward stretching of the tube 12 to accommodate the plug 2. Meanwhile, in some embodiments, the implant 1 may be implanted without the addition of the plug 2.

Figure 5:
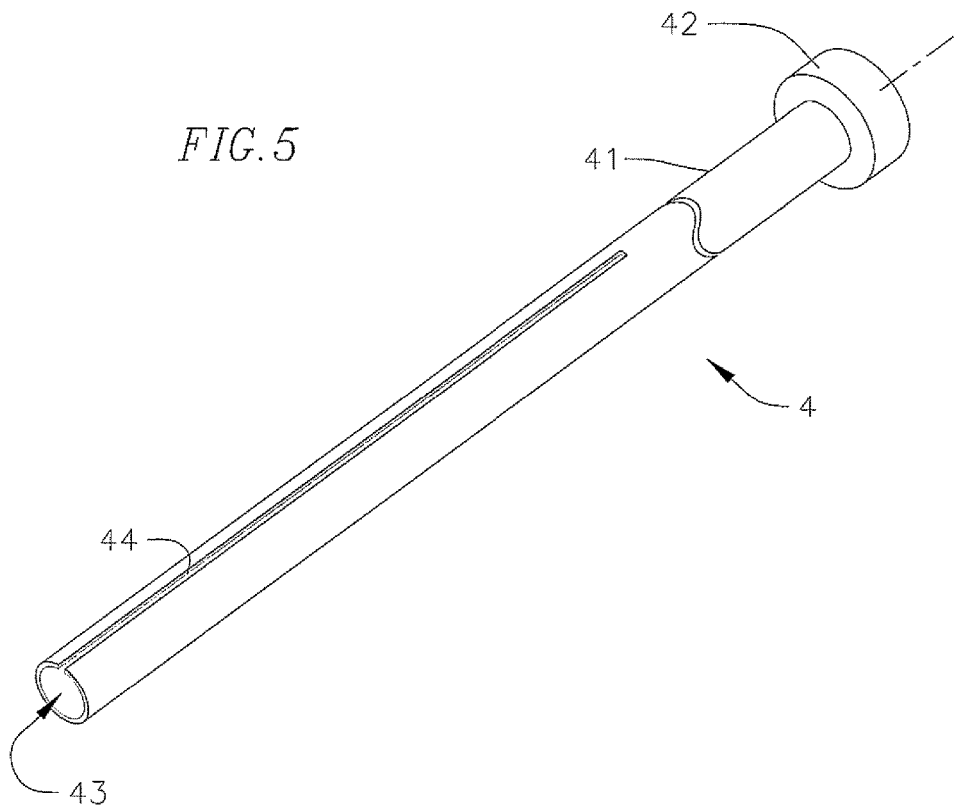
FIG. 5 is a perspective view of a pusher tool according to an embodiment of the invention.
Figure 6:
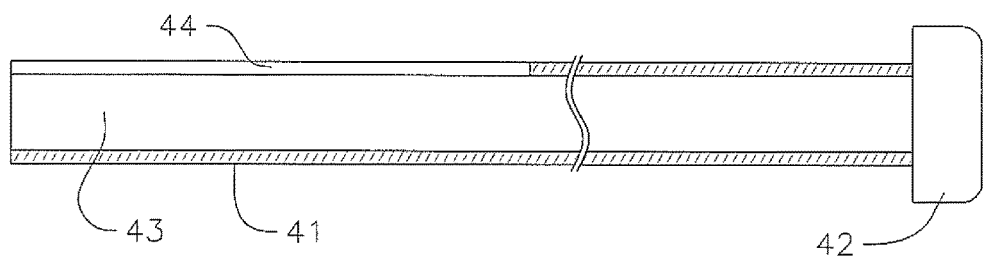
FIG. 6 is a cross-sectional view of the pusher tool of FIG. 5.

FIGS. 3 and 4 show a holding and/or delivery means, for example, a delivery device such as a sheath 3 for implanting a wound closure implant 1 according to an embodiment of the invention. FIGS. 5 and 6 show a pushing or advancing means, for example, a pusher device or tool 4 for advancing the wound closure implant 1 through the delivery sheath 3 according to an embodiment of the invention.

The delivery sheath 3 is a catheter device used to position and deploy the wound closure implant 1. In the illustrated embodiment, the delivery sheath 3 has a substantially cylindrically shaped tubular portion 31, which may be made of or include one or more suitable polymers, for example, polypropylene, and which has an outer diameter of about 20 French. At a proximal end of the tubular portion 31, the delivery sheath 3 may further include a grip 32, which may be in some embodiments a heat shrink grip that is fixed to the tubular portion 31. The tubular portion also defines a coaxial inner bore 33 extending therethrough, where the bore may have an inner diameter of about 18 French. An entire length of the delivery sheath 3 may be approximately 30 centimeters.

Meanwhile, the pusher tool 4 is sized to be inserted into the bore 33 of the delivery sheath 3, thereby providing a delivery system for the implant. The pusher tool 4 also includes a cylindrically shaped tubular portion 41, which may be made of or include one or more suitable polymers, for example, polyether block amide (for example, PEBAX® polyether block amide (Arkema, Colombes, France)) and/or polyethylene, and which may have an outer diameter slightly smaller than the inner diameter of the delivery sheath 3. For example, the tubular portion 41 of the pusher tool 4 may have an outer diameter of about 17.5 French when the inner diameter of the delivery sheath 3 is about 18 French. At a proximal end of the tubular portion 41, the pusher tool 4 may further include a compression cap 42, which may be attached to the tubular portion 41 via, for example, a polycarbonate Luer fitting or connector. The pusher tool 4 is generally longer in length than the delivery sheath 3, and in the instant embodiment, is approximately 40 centimeters. In addition, the tubular portion 41 of the pusher tool 4 defines a coaxial inner bore 43 which extends therethrough. The inner diameter of the tubular portion 41 in the instant embodiment is about 12.5 French, but in general, should be sized to readily accommodate the elastic tube 12 of the implant 1 when the tube 12 is compressed or collapsed radially, as well as a guide wire (not shown) passing through the implant 1. The tubular portion 41 of the pusher tool 4 may also include an additional longitudinal slit 44, which extends from a distal end towards the proximal end of the pusher tool 4 over, for example, about 15 centimeters of the tubular portion 41. In some embodiments, the length of the slit 44 corresponds substantially to the length of the tube 12 of the implant 1, and may facilitate easier loading or insertion of the elastic tube 12 of the implant 1 into the pusher tool 4.

Figure 7:
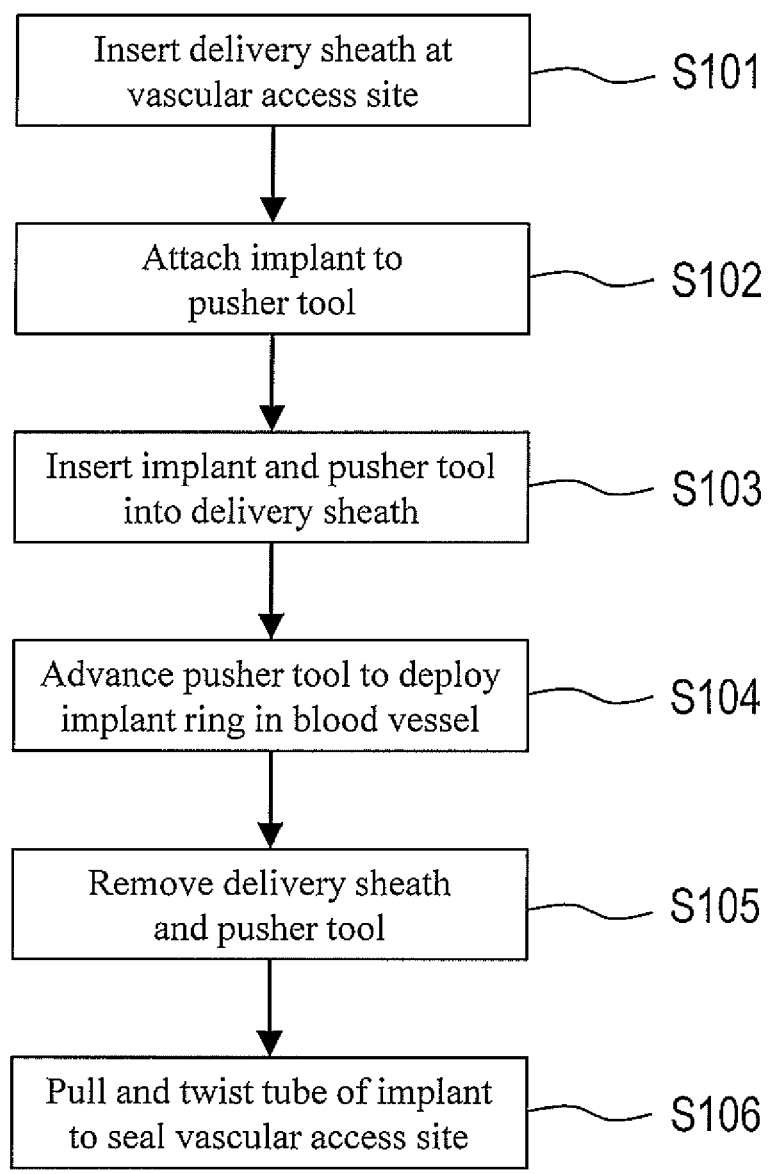
FIG. 7 is a flow chart illustrating a method of implanting a wound closure device according to an embodiment of the invention.

FIG. 7 illustrates a block diagram flow chart illustrating a method of implanting a wound closure device to close a wound opening at a vascular access site according to one embodiment of the invention. In some embodiments, the wound opening has a width greater than about 14 French. FIGS. 8-12 illustrate various steps in a method of implanting a wound closure device according to another embodiment of the invention.

After carrying out a procedure in which a wound opening, for example, an arteriotomy hole or vascular access site is formed in a blood vessel, such as for a percutaneous delivery of a prosthetic heart valve, the tools utilized for the initial procedure are first removed from the vascular access site. In some embodiments, a guide wire may remain from the initial procedure and may be utilized for the delivery of the wound closure device, or a different or additional guide wire may be inserted prior to delivery of the wound closure device.

In step S101 of FIG. 7, a delivery sheath is inserted at the vascular access site. The delivery sheath may be deployed along a guide wire previously inserted or left behind from an initial procedure or along a new guide wire. At least a distal tip of the delivery sheath is inserted through the arteriotomy hole in the wall of the blood vessel, and into the blood vessel. In step S102, the implant of the wound closure device (e.g., implant 1 as seen in FIG. 1) is attached to the pusher tool 4. Referring back to FIGS. 1-6, attachment of the implant 1 to the pusher tool 4 may include collapsing or compressing the tubular portion 12 of the implant 1 (e.g., manually by pinching or other means) and inserting the tubular portion 12 into the bore 43 of the pusher tool 4. In embodiments where the pusher tool 4 has a slit 44, the tubular portion 12 of the implant 1 can be inserted into the bore 43 through the slit 44, for example, by manually expanding the slit 44. Generally, the implant 1 will be attached to the pusher tool 4, such that the ring 11 of the implant 1 remains on an outside of the pusher tool 4 and rests against or is adjacent to the distal end of the pusher tool 4. Generally, ring 11 of implant 1, even when collapsed, is oversized relative to pusher tool 4, so that it will not fit into the bore 43. In embodiments in which a guide wire is used, the guide wire will pass through centers of both the implant 1 and the pusher tool 4. In step S103, the implant 1 and the pusher tool 4 are inserted at a proximal end of the delivery sheath 3 into the bore 33 of the delivery sheath 3. Here, the ring 11 of the implant 1 is compressed to fit into the bore 33 of the delivery sheath 3. The pusher tool 4 is then advanced through the bore 33 of the delivery sheath 3 to advance or push the implant 1 towards the distal opening of the delivery sheath 3.

Figure 8:
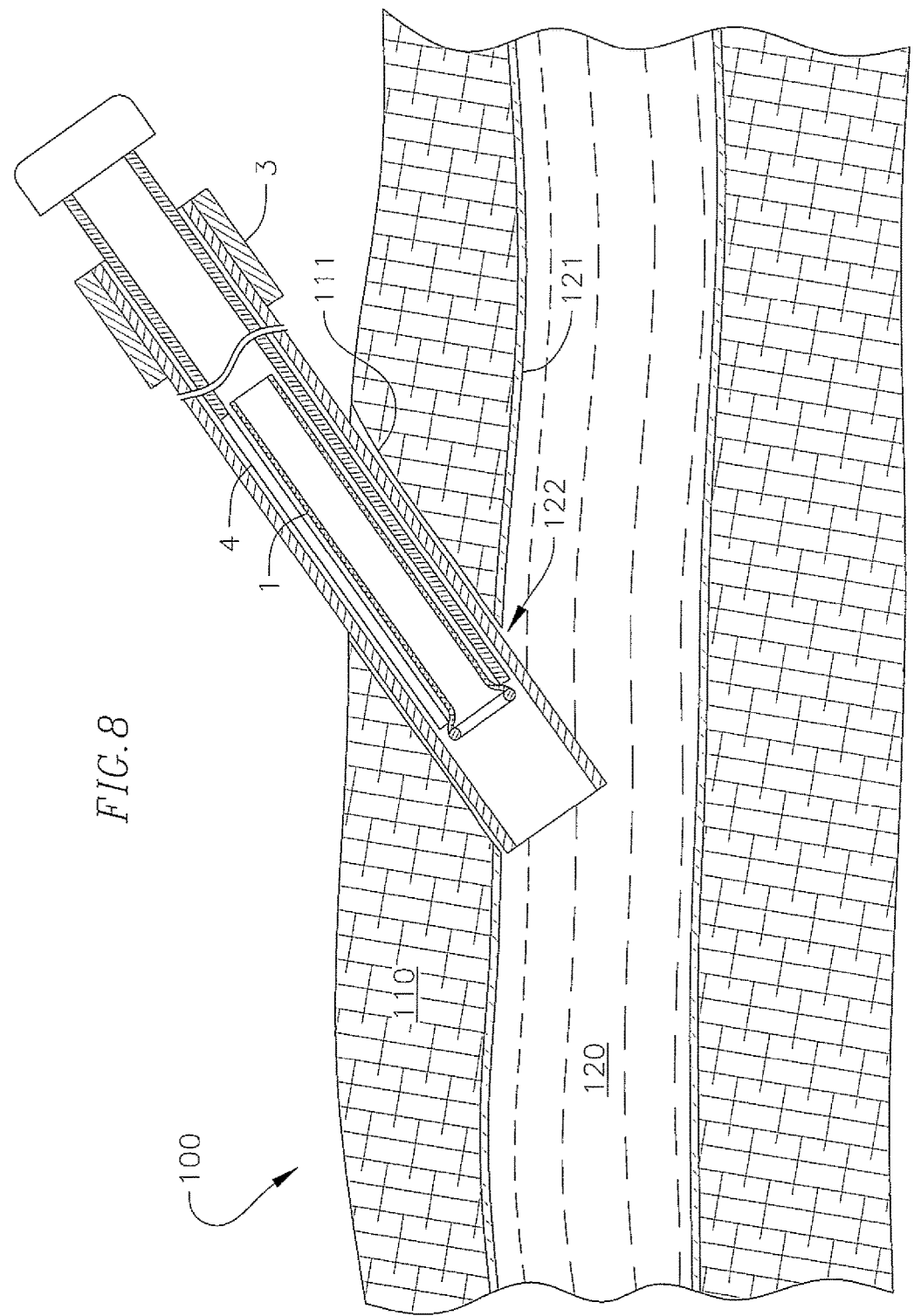
FIGS. 8-12 illustrate method steps of implanting a wound closure device according to another embodiment of the invention.
Figure 9:
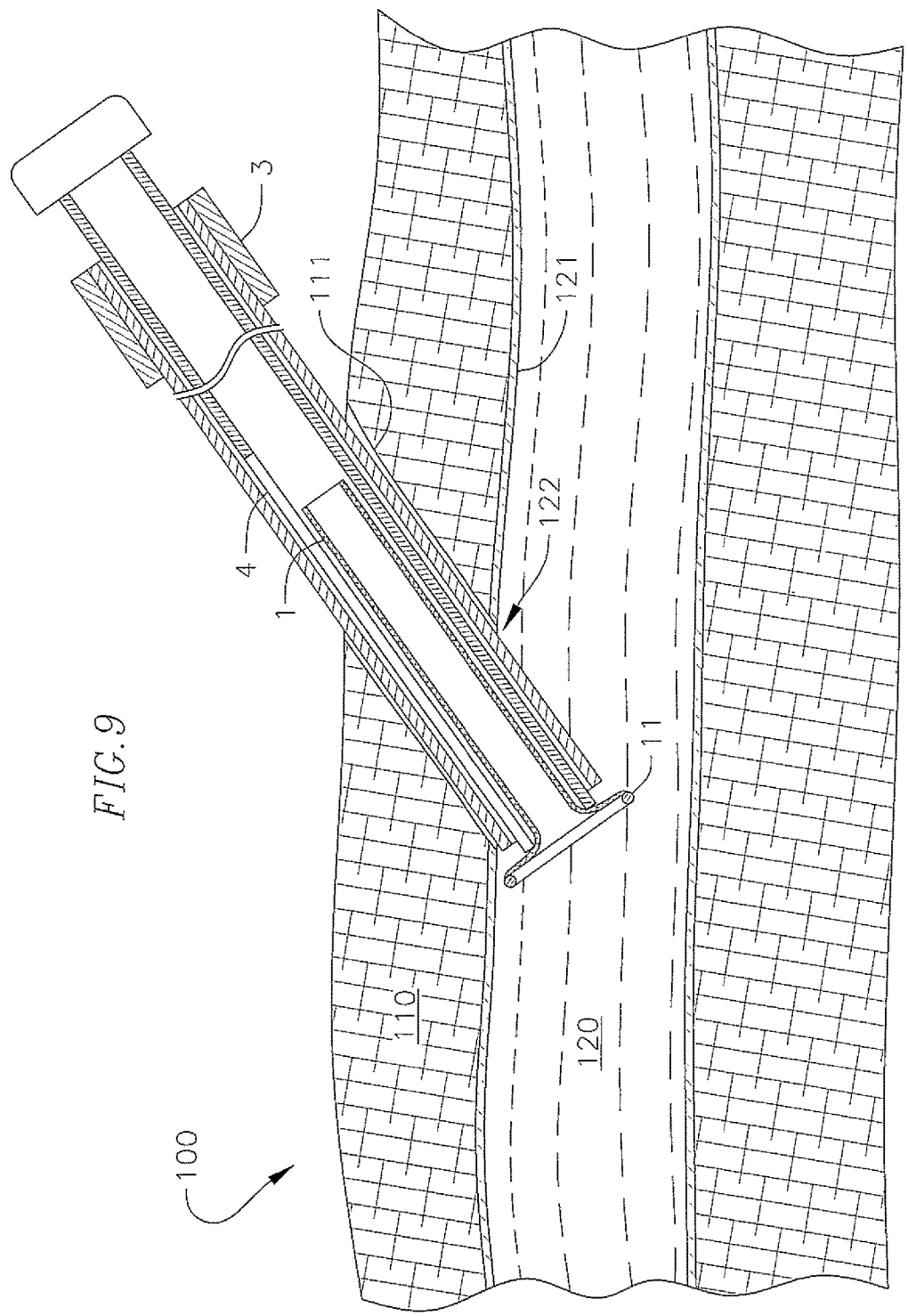

In some embodiments of deployment methods, as discussed above, the delivery sheath 3 may already be positioned at the vascular access site first, prior to attachment of the implant 1 to the pusher tool 4 and insertion of the implant 1 and the pusher tool 4 into the delivery sheath 3, so that the implant 1 and pusher tool 4 are inserted into the delivery sheath 3 while the delivery sheath 3 is already positioned in a patient's body. In other embodiments, the implant 1, pusher tool 4, and delivery sheath 3 may first be preassembled together, prior to inserting the delivery sheath 3 at the vascular access site. FIG. 8 illustrates an embodiment in which the delivery sheath 3, the pusher tool 4, and the implant 1 are advanced together to a vascular access site. In FIG. 8, the delivery sheath 3 with the pusher tool 4 and implant 1 are advanced through a tissue tract 111 of the tissue 110 of body 100 to blood vessel 120. A distal tip of delivery sheath 3 is advanced through an opening 122 in the vessel wall 121 and into the lumen of blood vessel 120. The advancement of the implant 1 and delivery tools 3, 4 may be along a guide wire in some embodiments, as previously discussed.

Then, in step S104, the pusher tool 4 is advanced further into the delivery sheath 3 via, for example, pressure applied at compression cap 42. The pusher tool 4 is advanced until the ring 11 of the implant 1 is moved past and out of the opening at the distal end of the delivery sheath 3 and into the lumen of the blood vessel 120 on a distal side of the vessel wall. After the ring 11 of the implant 1 is no longer radially compressed by the inner wall of the delivery sheath 3, the ring 11 is allowed to expand in the lumen of the blood vessel 120. The relative size of the ring 11 of the implant 1 in its expanded state is generally selected to be larger than the greatest diameter or width of the arteriotomy hole that is to be sealed. The ring 11 of the implant 1 may be configured to expand itself upon exiting the delivery sheath 3, or may be configured to expand upon actuation by a practitioner or other user. Expansion of the ring 11 of the implant 1 can be seen, for example, in FIG. 9.

After the ring 11 of the implant 1 exits the delivery sheath 3 into the lumen of the blood vessel 120 and is allowed to expand, in step S105, the delivery sheath 3 and the pusher tool 4 are removed from the vascular access site. The implant 1 remains at the vascular access site after removal of the delivery tools 3, 4 in an open or second position in which the bore of the tubular portion 12 is open from the first portion 18 to the second portion 19 thereof. The ring 11 of the implant 1 in its expanded state may be pushed or pulled against an inner surface of the vessel wall 121 of the blood vessel 120, and is prevented from escaping through the opening 122 by virtue of the oversize of the ring 11 relative to the opening 122. Therefore, when the pusher tool 4 is pulled away from the vascular access site, the ring 11 holds the implant 1 in position at the vascular access site and prevents the implant 1 from also being removed from the tissue tract 111, and the portion of the tube 12 of the implant 1 that was held in the bore 43 of the pusher tool 4 is drawn out of the pusher tool 4. Furthermore, after removal of the delivery tools 3, 4, the ring 11 of the implant 1 may be held against the wall 121 of the blood vessel 120 from the luminal side by the pressure inside the blood vessel 120, which will naturally push the ring against the wall 121 of the blood vessel 120. In some embodiments, additional frictional or holding means, such as frictional elements, may be located on the ring 11 or tube 12 to hold the ring 11 and/or the distal end of the tube 12 in this position. In addition, a length of the tubular portion 12 of the implant is generally selected, such that the tubular portion 12 is long enough to extend entirely through the tissue tract 111 adjacent to the vascular access site and to an outside of the body 100, for easier access by a practitioner or other user.

Figure 10:
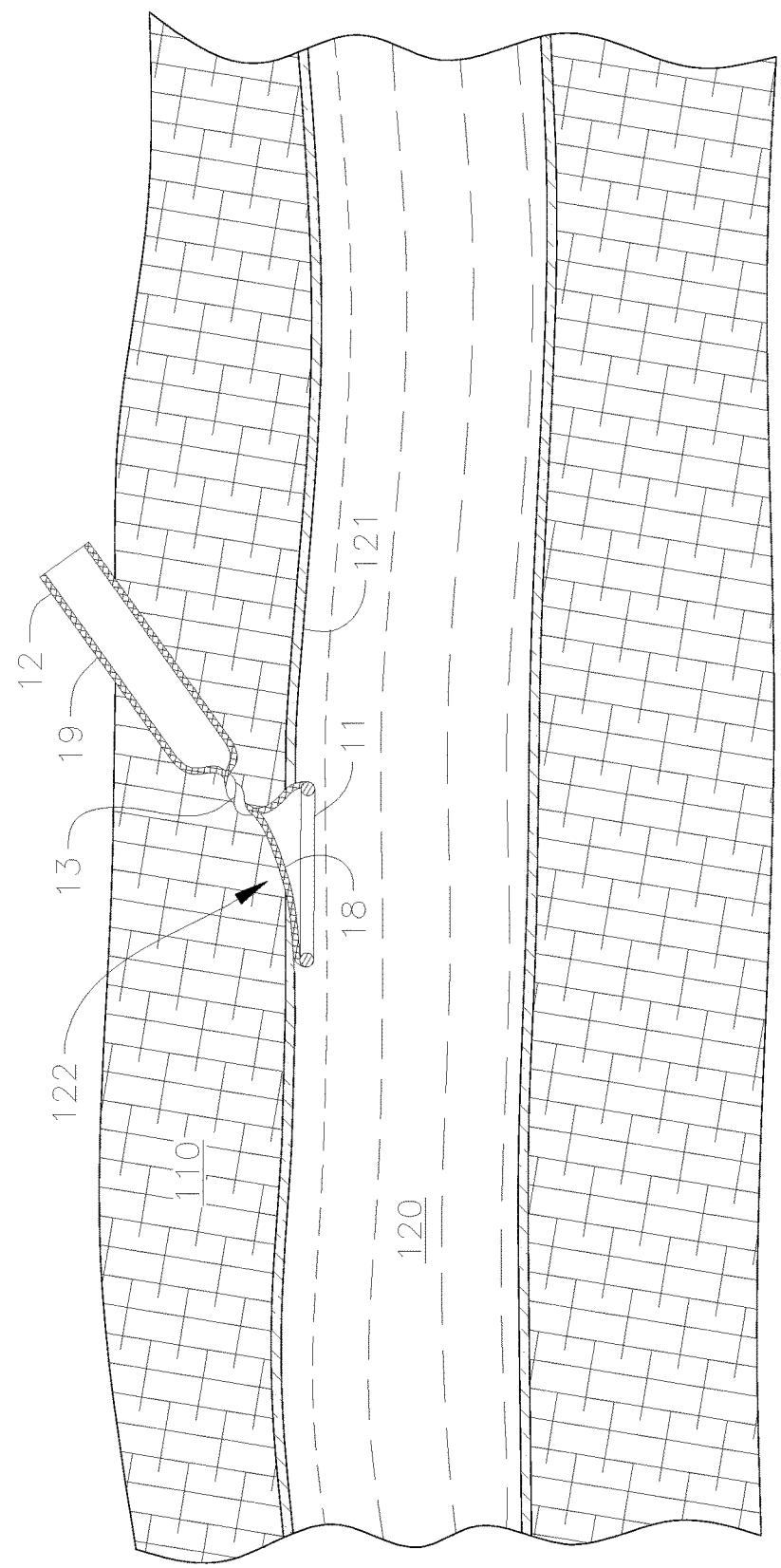

As seen in step S106 and as illustrated in FIG. 10, after removal of the delivery tools 3, 4 from the vascular access site, the tubular portion 12 of the implant 1 may be pulled from the second end 16 on the proximal side of the vessel wall 121 to further tension the ring 11 of the implant 1 against the wall 121 of the blood vessel 120. The second portion 19 of the tubular portion 12 of the implant 1 is then twisted or rotated circumferentially around the longitudinal axis of the implant 1 relative to the first portion 18 to create a twist seal 13 in the tubular portion 12 of the implant 1 between the first portion 18 and the second portion 19 of the tubular portion 12, resulting in a closed or first position of the implant 1. In the illustrated embodiment, the twist seal 13 is adjacent or near the ring 11 and the blood vessel wall 121. The twist seal 13 closes the bore or lumen of the implant 1 and seals the opening 122. Converting the implant from the second position to the first position by twisting the tubular portion 12 also reduces a length of the implant 1 in the illustrated embodiment.

The twist seal 13 may further form a substantially flat disc or surface in the implant 1 at or near the ring 11, which blocks the opening 122 in the vessel wall 121 and prevents or restricts blood from flowing out of the opening 122, where the ring 11 forms a perimeter of the disc and the tubular portion 12 converges at the twist seal near a center of the disc. By twisting the tubular portion 12 and forming a disc or substantially flat surface at the ring 11, the implant 1 may reduce or prevent clots from otherwise forming in a portion of the implant 1 recessed from the ring 11.

In some embodiments, the tubular portion of the implant may further include one or more longitudinal stiffener strands to facilitate the twisting, or to aid in holding the implant in the twisted state (first position) after the twisting step. In some embodiments, such stiffener strands or other parts of the tubular portion may be made of or include, for example, a superelastic nickel-titanium alloy (nitinol) or other shape memory material, where the twisted configuration of the tubular portion represents its unstressed state at, for example, body temperature. In such embodiments, the implant may be cooled or held open or untwisted during implantation, and then allowed to return to its unstressed, twisted, state after the distal end has been placed in a desired position.

Some embodiments of the implant may also include additional frictional elements on its surface, for example, along part or all of the tubular portion. These frictional elements could be used to hold the implant in its twisted configuration and prevent, for example, untwisting of the implant after twisting. Such frictional elements may allow for easy rotation of the tubular portion in one direction, for example, in a clockwise direction, to effect the twisting seal, but the frictional elements may engage the surrounding tissue to prevent or otherwise hinder movement of the tubular portion in the opposite direction, for example, in a counterclockwise direction. This may assist in locking the implant in its final twisted configuration and prevent the implant from inadvertently untwisting and opening back up after implantation.

Figure 11:
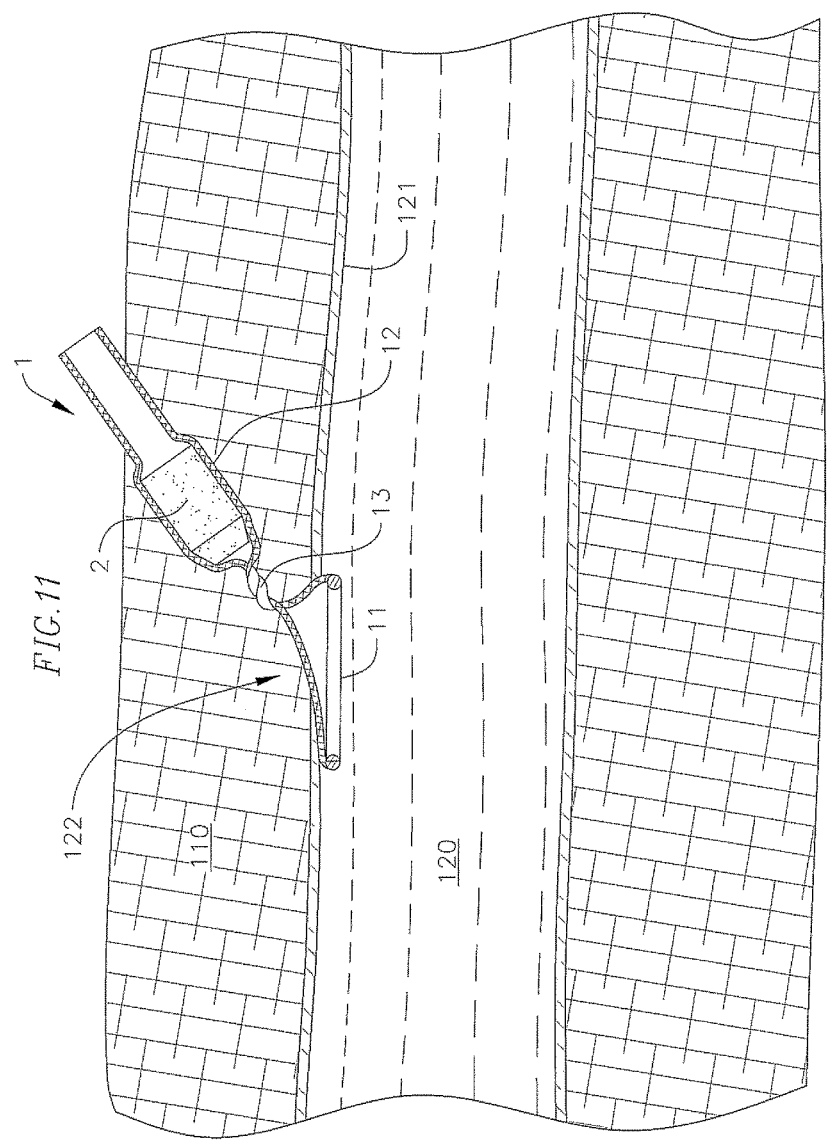
Figure 12:
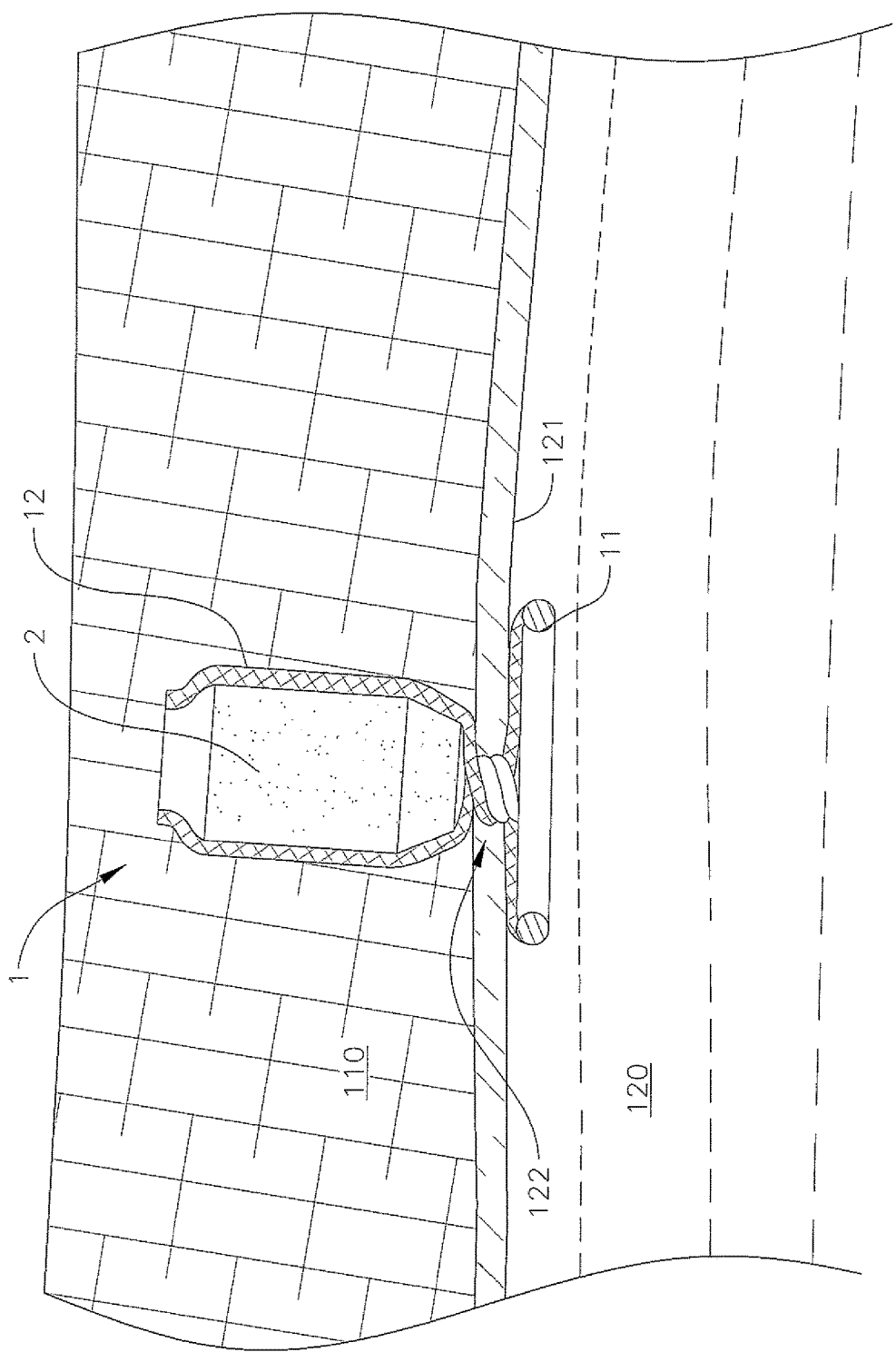

Then, in embodiments in which a plug 2 is utilized, as illustrated in FIGS. 11 and 12, the plug 2 is advanced into and through the second portion 19 of the tubular portion 12 of the implant 1 towards the twist seal 13, until further advancement is hindered or prevented by the twist seal 13 (e.g., manually or using a pusher device). In embodiments where the plug is made of or includes collagen, the plug 2 may expand upon contact with blood or other bodily fluids, or with user applied fluid (for example, saline) once inserted into the tissue tract 111. Meanwhile, the twist seal 13 prevents the plug 2 from being inadvertently pushed into the blood vessel 120. Generally, advancement of the plug 2 may also serve to shorten the device, and more specifically, to shorten a space between the ring 11 and the plug 2, which each has a larger diameter or width compared to the twist seal 13. The shortening of the space between the ring 11 and plug 2 serves to provide a compressive force on the blood vessel wall 121 and/or the surrounding tissue 110, in order to further aid in sealing and/or healing of the access site. As illustrated in FIG. 12, the wall 121 of the blood vessel 120 around the opening 122 is pinched or sandwiched between the ring 11 of the implant 1 and the plug 2, where the plug 2 provides a tensile force to help securely hold the ring 11 of the implant 1 against the inner surface of wall 121 of the blood vessel 120, and also may contribute to the seal by applying the compressive pressure against an outer surface of wall 121 of the blood vessel 120 and/or the surrounding tissue 110. Here, the plug 2 is positioned in the tissue tract 111 and may further be held in place, for example, by radially inward pressure applied by the tissue 110 against the tubular portion 12 of the implant and the plug 2. In the final configuration of this embodiment, the plug 2 serves to seal the tissue tract 111, and may further aid in sealing any leaks, such as micro leaks, from the blood vessel 120 that leak past or around the ring 11 or through the tubular section 12 of the implant 1. After the plug 2 is moved to a desired final position, in some embodiments, the tubular section 12 may be cut or otherwise shortened, so that the proximal end of the tubular section 12 no longer extends outside of the body.

Another embodiment of the wound closure device is illustrated in FIGS. 13-16. The device illustrated in FIGS. 13-16 does not include a plug, but instead includes a single implant 21 with two ends 22 and a central portion. In some embodiments, the ends 22 are identical, and may be or include rings or frames similar to the ring 11 described in the embodiment above. In other embodiments, the end rings may be rigid rings that are not radially collapsible. In yet other embodiments, the ends may be configured differently, for example, where a first ring may be radially collapsible to facilitate easier insertion into a wound access site, while a second ring is configured to be more rigid.

Figure 14:
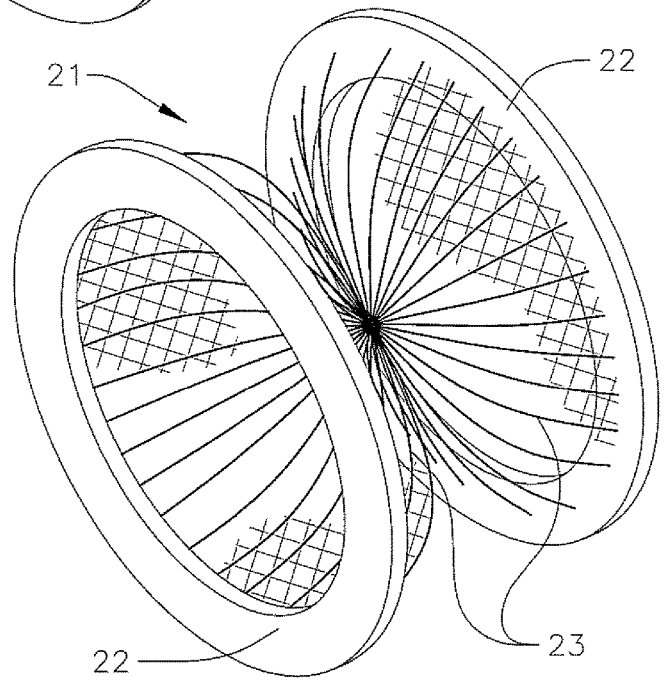

The central portion of the implant 21 may include relatively stiff strands 23 for maintaining a desired shape or structure of the implant 21. In some embodiments, the strands 23 may be made of or include, for example, nitinol, or another shape memory alloy or other material, where a twisted configuration forming a central twist seal (e.g., as illustrated in FIG. 14) represents an unstressed state of the implant 21 at, for example, body temperature. In these embodiments, the implant 21 may be cooled or held open or untwisted by an outside force during implantation, and then allowed to return to its unstressed, twisted orientation, after implantation. In other embodiments, the strands 23 may not include a shape memory material, but rather may include a stiffer material that can be bent or otherwise deformed to better hold the implant 21 in a twisted configuration shown in FIG. 14 after implantation and manual twisting, for example, by a practitioner or implantation device.

In some embodiments, the implant 21 may further include a tubular section comprising a mesh or other relatively softer material similar to the mesh described above in the first embodiment. In some embodiments, the mesh or other material may surround the entire implant 21, or may only cover, for example, the strands 23. In other embodiments, the mesh may or other material instead be attached to the ends 22 and/or the strands 23 to cover or seal the recesses or gaps located between the ends 22 and the strands 23.

As indicated above, parts of the implant 21 may be made of or include nitinol or other shape memory alloy, or another material. Alternatively, some parts of the implant 21 may be made of or include other biocompatible metal, alloy, or other suitable material. Meanwhile, other portions of the implant 21, for example, a mesh of the implant 21 and/or rings positioned at the ends 22 of the implant 21, may be made of or include a bioabsorbable polymer or other bioabsorbable material, similar to the materials discussed above with respect to the first embodiment.

Figure 15:
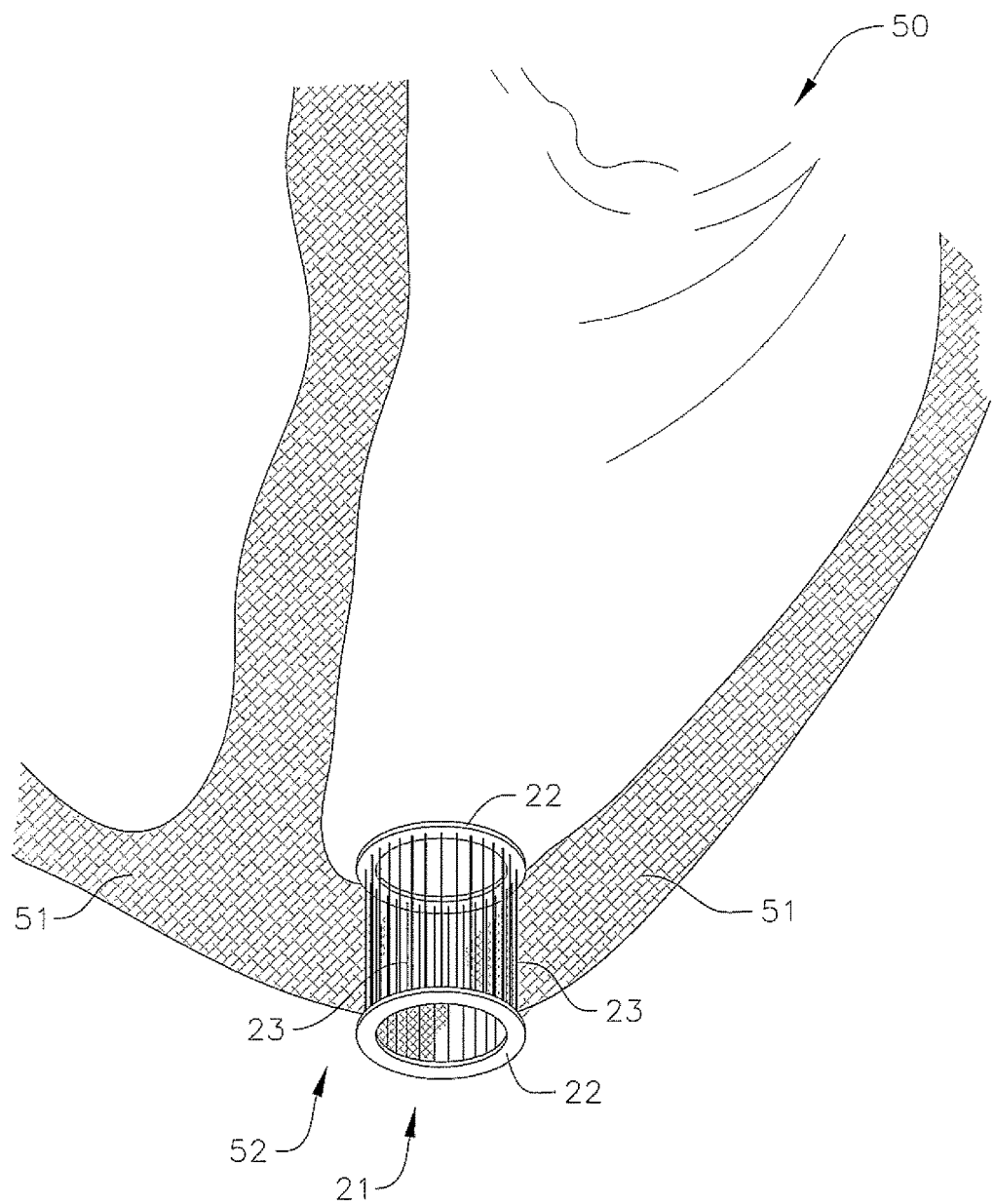
FIGS. 15-16 illustrate steps of implanting the wound closure device of FIGS. 13-14.
Figure 16:
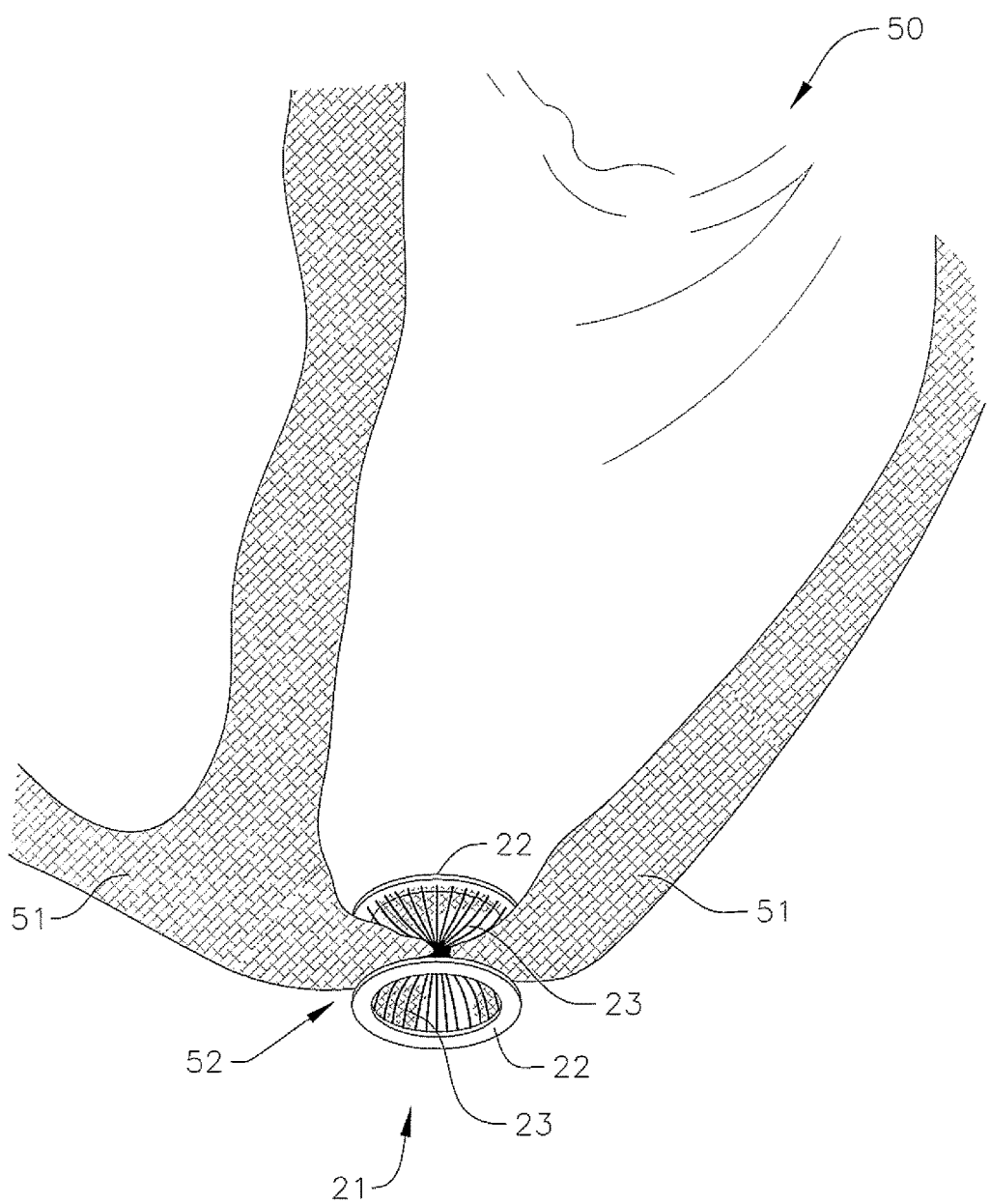

Referring now to FIGS. 15 and 16, the implant 21 according to this embodiment can be implanted, for example, at an apical access site 52 located in a heart wall 51 at or near an apex of a heart 50. After a procedure in which apical access into a heart is required, the implant 21 can be used to seal or close the access site 52 at the apex of the heart.

First, in FIG. 15, the implant 21 is positioned in the access site 52, where a distal first end 22 of the implant is inserted through the access site 52 to an inside of the heart 50. In some embodiments, a ring on the distal end 22 of the implant may be radially collapsible to facilitate insertion of the implant 21 through the access site 52, where the ring can then be expanded to its original size after passing through the access site 52. In embodiments in which the implant 21 is twisted in its unstressed state, the implant 21 may first be cooled, manually untwisted, or otherwise manipulated, so that it is in its untwisted state (as seen, e.g., in FIG. 13), during insertion.

Then, in FIG. 16, the implant is twisted to its final configuration in the access site 52. Here, the twisting of the implant 21 creates an effective twist seal. For example, in embodiments in which a shape memory material is used, the strength of the twist seal can be established and tested prior to implantation. As seen with the first embodiment, the twisting of the implant 21 also creates a flatter surface at the ends 22, such that space where unwanted clots could potentially form can be reduced or minimized. Finally, as can be seen in FIG. 16, the twisting of the implant 21 also shortens the implants and draws the two ends 22 closer to one another and reduces a space between the two ends 22. This may create a compressive or pinching force on the heart wall 51, which may further aid in healing of the tissue around the access site 52 and anchoring of the implant 21.

Figure 13:
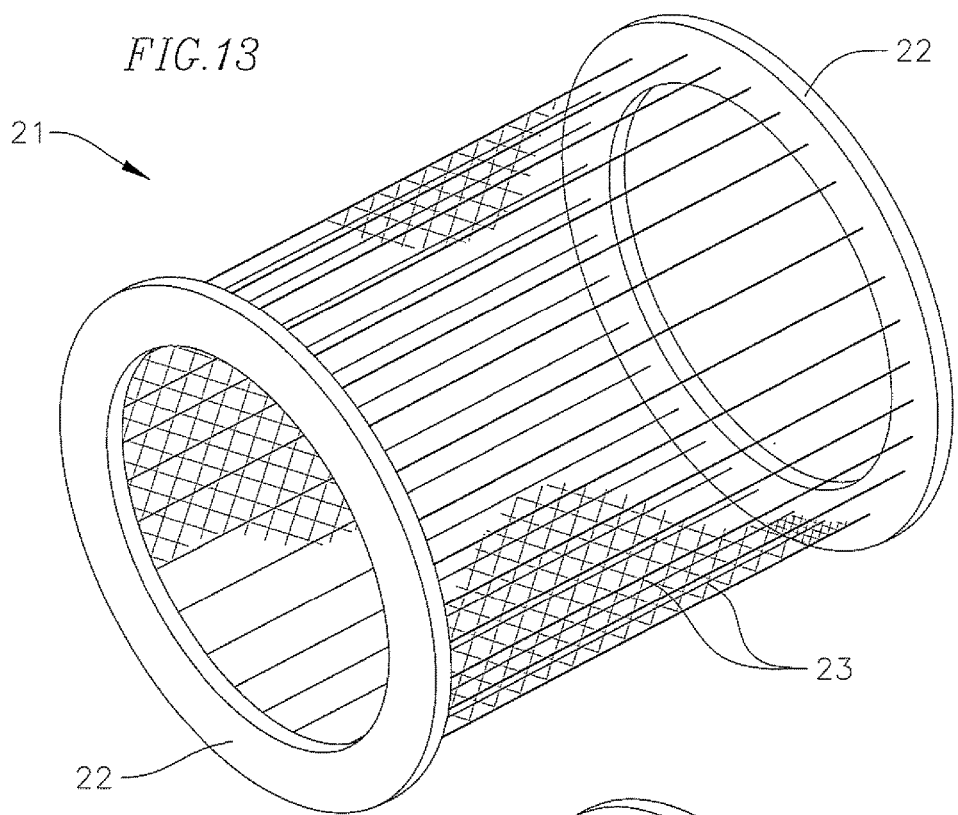
FIGS. 13-14 show a wound closure device according to yet another embodiment of the invention.

Furthermore, similarly as discussed with the first embodiment, the implant 21 in FIGS. 13-16 may also include frictional elements on some or all of its exterior surface, which allows for easy or preferential rotation of the implant 21 to its final twisted configuration, shown in FIGS. 14 and 16, while preventing or making more difficult rotation of the implant 21 back to its open configuration shown in FIGS. 13 and 15.

Some embodiments of the wound closure device described above may also be used interchangeably between different types of wounds. For example, the wound closure device described in FIGS. 1-6 may be used for an access site in a heart wall, where the plug can serve as an enlarged proximal end of the implant. In such application, the plug may be inserted at least past an outer surface of the heart wall. Similarly, the wound closure device described in FIGS. 13-14 may be used for vascular access sites in some applications.

Various other modifications of the embodiments described are also conceivable. For example, for the implants, the shape or configuration of the frame or ring at the distal end can be modified in various ways for better sealing of the specific application, such as for arteriotomy holes or for an apical access site in a heart wall. In other embodiments, barbs or anchors or other features can be molded into the frame or ring to facilitate a more secure attachment to the inner wall of the blood vessel or the heart wall. In some embodiments utilizing a plug, the tubular portion can be modified, for example, with an outer rail design, to allow for the plug or other plugging or stabilization means to ride over or around the tube, rather than be inserted through the tube. Various other modifications may also be implemented.

Embodiments of the invention provide a wound closure device and a method for closing access sites such as large arteriotomy holes or access sites made in a heart wall in a less invasive and more effective manner. More specifically, some embodiments of the invention provide a percutaneous solution for closing puncture sites in, for example, walls of blood vessels, that are up to or greater than about 30 French in diameter, while other embodiments of the invention provide a solution for safely and effectively closing an apical access site in a heart wall. The device and method can further be applied efficiently, and in some instances, can be effectively applied in a matter of seconds. The elasticity of the device helps the device conform to the vessel wall, the heart wall, and/or the tissue tract in an effective manner upon implantation. In addition, the device and method according to embodiments of the invention provide for an atraumatic solution for closing a wound that does not require suturing or stapling, and also does not require further dilation of the puncture site to achieve hemostasis. In addition, if hemostasis is not initially achieved with the implant, in embodiments where a guide wire is utilized, the blood vessel or access site on the heart can still be easily re-accessed for reapplication of the implant. Furthermore, in embodiments where the entire implant is made of bioabsorbable materials, there would be no sutures, staples, or other parts of the implant left behind over time, since the entire implant would be dissolved by the body, and the healed vessel or wall would be available for re-access at the access site if needed.

While the present disclosure has been described in connection with certain exemplary embodiments, it is to be understood that the disclosure is not limited to the particular embodiments and examples, but is instead intended to cover various modifications and equivalent arrangements included within the spirit and scope of the appended claims, and equivalents thereof.

What is claimed is:

1. A method for closing a wound opening in a heart wall or a vessel wall of a patient's body with an implant having a first end, a second end, and a longitudinal axis extending between the first end and the second end, the implant comprising a frame at the first end and a flexible tubular section connected to the frame and extending along the longitudinal axis, wherein a wall of the tubular section defines a coaxial inner bore, the method comprising:
   inserting the frame of the implant through the wound opening and positioning the frame on a distal side of the heart wall or the vessel wall, wherein a width of the frame is greater than a width of the wound opening;
   rotating a second portion of the tubular section circumferentially around the longitudinal axis from a proximal side of the heart wall or the vessel wall while a first portion of the tubular section is held against rotation, the rotation forming a twist seal at an area of the tubular section between the first and second portions to close the bore; and
   inserting a plug into the coaxial inner bore of the tubular section from the second end of the implant and advancing the plug along the longitudinal axis towards the twist seal and frame at the first end of the implant, wherein the twist seal is positioned after the plug along the longitudinal axis and before the frame along the longitudinal axis.

2. The method of claim 1, wherein the wound opening has a width greater than 14 French.

3. The method of claim 1, wherein the wound opening and a portion of the heart wall or the vessel wall defining the wound opening are positioned between the frame of the implant and the plug.

4. The method of claim 1, further comprising inserting the implant via a delivery tool, wherein the frame of the implant is compressed in the delivery tool, wherein the delivery tool is inserted through the wound opening prior to insertion of the frame of the implant through the wound opening, and wherein the implant is advanced out of the delivery tool to expand the frame of the implant on the distal side of the heart wall or the vessel wall.

5. The method of claim 1, wherein advancing the plug includes applying a compression force of a first end of the plug against the heart wall or the vessel wall.

6. The method of claim 1, further comprising cutting the second end of the implant such that the second end does not extend outside of the patient's body.

7. The method of claim 1, wherein inserting the plug occurs after the twist seal is formed, and further wherein inserting the plug occludes the coaxial inner bore.

8. The method of claim 1, wherein the plug has a diameter that is greater than a resting diameter of the flexible tubular section such that when the plug is inserted into the tubular section, the plug causes the tubular section to expand radially to accommodate the plug.

9. The method of claim 1, wherein advancing the plug reduces a distance between the frame at the first end of the implant and the plug.

10. A method for closing a wound opening in a heart wall or a vessel wall with an implant having a first end, a second end, and a longitudinal axis extending between the first end and the second end, the implant comprising a frame at the first end and a flexible tubular section connected to the frame and extending along the longitudinal axis, wherein a wall of the tubular section defines a coaxial inner bore, the method comprising:

inserting the frame of the implant through the wound opening and positioning the frame on a distal side of the heart wall or the vessel wall, wherein a width of the frame is greater than a width of the wound opening;

rotating a second portion of the tubular section circumferentially around the longitudinal axis from a proximal side of the heart wall or the vessel wall while a first portion of the tubular section is held against rotation, the rotation forming a twist seal at an area of the tubular section between the first and second portions to close the bore at the twist seal; and inserting a plug into the coaxial inner bore of the tubular section from the second end of the implant after the twist seal is formed, wherein the plug is spaced from the twist seal along the longitudinal axis and wherein the plug occludes the coaxial inner bore.

11. The method of claim 10, further comprising advancing the plug in the tubular section towards the twist seal, wherein advancing the plug includes applying a compression force of a first end of the plug against the heart wall or the vessel wall.

\* \* \* \* \*